(12) United States Patent
Blalock

(10) Patent No.: US 9,254,118 B2
(45) Date of Patent: Feb. 9, 2016

(54) FLOATING TRANSDUCER DRIVE, SYSTEM EMPLOYING THE SAME AND METHOD OF OPERATING

(71) Applicant: Travis N. Blalock, Charlottesville, VA (US)

(72) Inventor: Travis N. Blalock, Charlottesville, VA (US)

(73) Assignee: Analogic Corporation, Peabody, MA (US)

( * ) Notice: Subject to any disclaimer, the term of this patent is extended or adjusted under 35 U.S.C. 154(b) by 273 days.

(21) Appl. No.: 13/844,275

(22) Filed: Mar. 15, 2013

(65) Prior Publication Data

US 2014/0276075 A1 Sep. 18, 2014

(51) Int. Cl.
*A61B 8/00* (2006.01)

(52) U.S. Cl.
CPC ............. *A61B 8/4494* (2013.01); *A61B 8/4483* (2013.01); *A61B 8/56* (2013.01)

(58) Field of Classification Search
CPC ................ B06B 1/0215; H03K 17/06; H03K 17/08122; H03K 17/6872; H03K 17/693; A61B 8/4494; A61B 8/56; A61B 8/4483
USPC ................................................. 600/437–469
See application file for complete search history.

(56) References Cited

U.S. PATENT DOCUMENTS

| 4,014,208 | A | * | 3/1977 | Moore | ..................... G01L 5/246 73/610 |
| 4,949,310 | A | | 8/1990 | Smith et al. | |
| 5,423,220 | A | * | 6/1995 | Finsterwald | .......... B06B 1/0622 310/322 |
| 5,817,024 | A | | 10/1998 | Ogle et al. | |
| 5,997,479 | A | | 12/1999 | Savord et al. | |
| 6,013,032 | A | | 1/2000 | Savord | |
| 6,126,602 | A | | 10/2000 | Savord et al. | |
| 6,135,961 | A | | 10/2000 | Pflugrath et al. | |
| 6,179,780 | B1 | | 1/2001 | Hossack et al. | |
| 6,203,498 | B1 | | 3/2001 | Bunce et al. | |
| 6,276,211 | B1 | | 8/2001 | Smith | |
| 6,380,766 | B2 | | 4/2002 | Savord | |
| 6,491,634 | B1 | | 12/2002 | Leavitt et al. | |
| 6,582,372 | B2 | | 6/2003 | Poland | |
| 6,641,534 | B2 | | 11/2003 | Smith et al. | |
| 6,669,641 | B2 | | 12/2003 | Poland et al. | |
| 6,894,425 | B1 | * | 5/2005 | Solomon | ................ B06B 1/0629 310/334 |
| 7,275,298 | B2 | * | 10/2007 | Schindel | ............... B06B 1/0292 216/62 |
| 2005/0154300 | A1 | * | 7/2005 | Wodnicki | ............... H04B 11/00 600/437 |
| 2007/0016022 | A1 | | 1/2007 | Blalock et al. | |
| 2007/0016044 | A1 | | 1/2007 | Blalock et al. | |
| 2008/0262357 | A1 | * | 10/2008 | Wodnicki | ............ G01S 7/52017 600/459 |
| 2010/0063399 | A1 | * | 3/2010 | Walker | ............... G01N 29/0654 600/459 |
| 2010/0312106 | A9 | | 12/2010 | Blalock et al. | |
| 2012/0262221 | A1 | * | 10/2012 | Bottarel | ................ B06B 1/0215 327/434 |
| 2012/0313689 | A1 | * | 12/2012 | Bottarel | ................ B06B 1/0215 327/434 |

* cited by examiner

*Primary Examiner* — Sanjay Cattungal
(74) *Attorney, Agent, or Firm* — Alan W. Cannon

(57) ABSTRACT

A floating transducer drive configured to isolate relatively low voltage system electronics from a relatively high voltage transmit circuit in an ultrasound imaging system. A receive circuit is electrically connected to an isolated local ground. An isolation circuit is electrically connected between the receive circuit and a relatively low-voltage processing circuit. The isolation circuit is configured such that during a transmit event during which the relatively high voltage transmit circuit sends a relatively high voltage signal to a transducer, the isolated local ground is electrically connected to the transmit circuit, but when the transmit event is not occurring, the isolated local ground is electrically connected to a system ground.

27 Claims, 10 Drawing Sheets

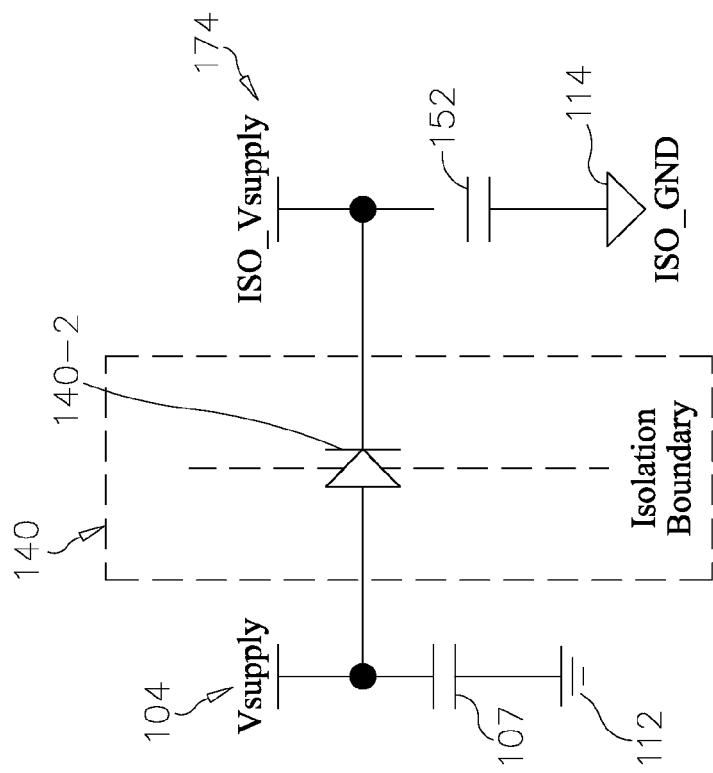
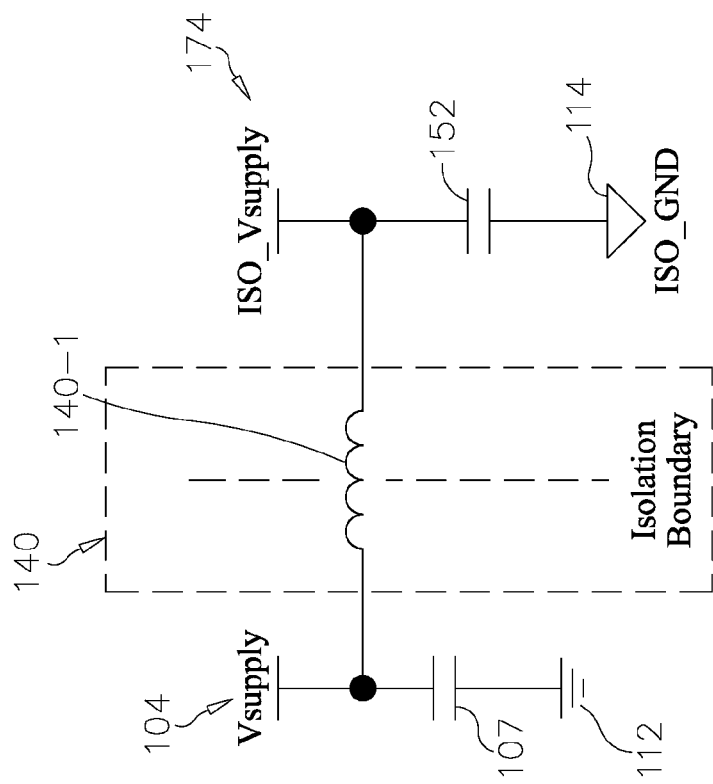
Fig. 4B
Fig. 4A

FLOATING TRANSDUCER DRIVE, SYSTEM EMPLOYING THE SAME AND METHOD OF OPERATING

FIELD OF THE INVENTION

The present invention relates to circuits, subsystems and methods for controlling transmission of signals to, and reception of signals from a transducer. More particularly, the present invention relates to circuits, subsystems and methods for controlling transmission of signals to, and reception of signals from a transducer in an ultrasound imaging system.

BACKGROUND OF THE INVENTION

Medical imaging is a field dominated by high cost systems that may be so complex as to require specialized technicians for operation and the services of experienced medical doctors and nurses for image interpretation. Medical ultrasound, which is considered a low cost modality, utilizes imaging systems costing as much as $250K, or more. These systems may be operated by technicians with two years of training or specialized physicians. This high-tech, high-cost approach works very well for critical diagnostic procedures. However it makes ultrasound impractical for many of the routine tasks for which it would be clinically useful.

A number of companies have attempted to develop low cost, easy to use systems for more routine use. One example of such an attempt is that by Sonosite. The Sonosite system produces very high quality images at a system cost of at least $20,000. While far less expensive than high-end systems, these systems are still very sophisticated and require a well-trained operator. Furthermore, at this price few new applications may be opened.

Many ultrasonic imaging systems utilize an array transducer that is connected to beamformer circuitry through a cable, and a display that is usually connected directly to or integrated with the beamformer. This approach is attractive because it allows the beamformer electronics to be as large as is needed to produce an economical system. In addition, the display may be of a very high quality.

Some conventional system architectures have been improved upon through reductions in beamformer size. One of the most notable efforts has been undertaken by Advanced Technologies Laboratories and then continued by a spin-off company, Sonosite. U.S. Pat. No. 6,135,961 to Pflugrath et al., entitled "Ultrasonic Signal Processor for a Hand Held Ultrasonic Diagnostic Instrument," hereby incorporated by reference herein in its entirety, describes some of the signal processing employed to produce a highly portable ultrasonic imaging system. The Pflugrath '961 patent makes reference to an earlier U.S. Pat. No. 5,817,024 to Ogle et al., entitled, "Hand Held Ultrasonic Diagnostic instrument with Digital Beamformer," hereby incorporated by reference herein in its entirety. In U.S. Pat. No. 6,203,498 to Bunce et al., entitled "Ultrasonic Imaging Device with Integral Display," hereby incorporated by reference herein in its entirety, however, the transducer, beamformer, and display may be all integrated to produce a very small and convenient imaging system.

Other references of peripheral interest are U.S. Pat. No. 6,669,641 to Poland, et al., entitled "Method of and system for ultrasound imaging," which is hereby incorporated herein, in its entirety, by reference thereto, which describes an ultrasonic apparatus and method in which a volumetric region of the body is imaged by biplane images. One biplane image has a fixed planar orientation to the transducer, and the plane of the other biplane image can be varied in relation to the fixed reference image.

U.S. Pat. No. 6,491,634 to Leavitt, et al., entitled "Sub-beam-forming apparatus and method for a portable ultrasound imaging," which is hereby incorporated herein, in its entirety, by reference thereto, describes a sub-beam-forming method and apparatus that is applied to a portable, one-dimensional ultrasonic imaging system. The sub-beam-forming circuitry may be included in the probes assembly housing the ultrasonic transducer, thus minimizing the number of signals that are communicated between the probe assembly and the portable processor included in the imaging system.

U.S. Pat. No. 6,380,766 to Savord, entitled "Integrated circuitry for use with transducer elements in an imaging system," which is hereby incorporated herein, in its entirety, by reference thereto, describes integrated circuitry for use with an ultrasound transducer of an ultrasound imaging system.

U.S. Pat. No. 6,013,032 to Savord, entitled "Beam-forming methods and apparatus for three-dimensional ultrasound imaging using two-dimensional transducer array," which is hereby incorporated herein, in its entirety, by reference thereto, describes an ultrasound imaging system including a two-dimensional array of ultrasound transducer elements that define multiple sub-arrays, a transmitter for transmitting ultrasound energy into a region of interest with transmit elements of the array, a sub-array processor and a phase shift network associated with each of the sub-arrays, a primary beam-former and an image generating circuit.

U.S. Pat. No. 6,126,602 to Savord, et al., entitled "Phased array acoustic systems with intra-group processors," which is hereby incorporated herein, in its entirety, by reference thereto, describes an ultrasound imaging apparatus and method that uses a transducer array with a very large number of transducer elements or a transducer array with many more transducer elements than beam-former channels.

U.S. Pat. No. 5,997,479 to Savord, et al., entitled "Phased array acoustic systems with intra-group processors," which is hereby incorporated herein, in its entirety, by reference thereto, describes an ultrasound imaging apparatus and method that uses a transducer array with a very large number of transducer elements or a transducer array with many more transducer elements than beam-former channels.

U.S. Pat. No. 6,582,372 to Poland, entitled "Ultrasound system for the production of 3-D images," which is hereby incorporated herein, in its entirety, by reference thereto, describes an ultrasound system that utilizes a probe in conjunction with little or no specialized 3-D software/hardware to produce images having depth cues.

U.S. Pat. No. 6,179,780 to Hossack, et al., entitled "Method and apparatus for medical diagnostic ultrasound real-time 3-D transmitting and imaging," which is hereby incorporated herein, in its entirety, by reference thereto, describes a medical diagnostic ultrasound real-time 3-D transmitting and imaging system that generates multiple transmit beam sets using a 2-D transducer array.

U.S. Pat. No. 6,641,534 to Smith, et al., entitled "Methods and devices for ultrasound scanning by moving sub-apertures of cylindrical ultrasound transducer arrays in two dimensions," which is hereby incorporated herein, in its entirety, by reference thereto, describes methods of scanning using a two dimensional (2-D) ultrasound transducer array.

U.S. Pat. No. 4,949,310 to Smith, et al., entitled "Maltese cross processor: a high speed compound acoustic imaging system," which is hereby incorporated herein, in its entirety, by reference thereto, describes an electronic signal processing device which forms a compound image for any pulse-echo ultrasound imaging system using a two-dimensional array transducer.

U.S. Pat. No. 6,276,211 to Smith, entitled "Methods and systems for selective processing of transmit ultrasound beams to display views of selected slices of a volume," which is hereby incorporated herein, in its entirety, by reference thereto, describes the selection of a configuration of slices of a volume, such as B slices, I slices, and/or C slices.

U.S. Patent Application Publication No. US 2010/0312106 to Blalock et al., entitled "Ultrasound Imaging Beam-Former Apparatus and Method, which is hereby incorporated herein, in its entirety, by reference thereto, describes an ultrasound imaging beamformer apparatus in which an incoming signal from a transducer is applied to an in-phase sample-and-hold and a quadrature sample-and-hold.

U.S. Patent Application Publication No. US 2010/0063399 to Walker et al., entitled "Front End Circuitry for Imaging Systems and Methods of Use," which is hereby incorporated herein, in its entirety, by reference thereto, describes front end circuitry including a receive circuit configured to receive signals generated using coded excitation, perform analog sampling the received electrical signals generated using coded excitation, and provide a weighted, summed digital signal by processing the analog samples.

U.S. Patent Application Publication No. US 2007/0016044 to Blalock et al., entitled "Ultrasonic Transducer Drive," which is hereby incorporated herein, in its entirety, by reference thereto, describes a shunt that is connectable between a receive side of an ultrasonic transducer and a reference potential. A signal generator may generate an outgoing signal during a period of time while the shunt connects the receive side of the transducer to the reference potential. A signal receiver may receive an incoming signal during a period while the shunt is substantially open.

U.S. Patent Application Publication No. US 2007/0016022 to Blalock et al., entitled "Ultrasonic Imaging Beam-Former Apparatus and Method," which is hereby incorporated herein, in its entirety, by reference thereto, describes an incoming signal from a transducer in an ultrasound imaging beam-formed apparatus that is applied to an in-phase sample-and-hold and a quadrature sample-and-hold.

A schematic diagram of a transducer drive 10 for a conventional phased array ultrasound system is shown in FIG. 1. A piezoelectric transducer array 12, shown on the left, acts as an interface to a signal processor by converting electrical signals to acoustic pulses and vice versa. Images may be formed by transmitting a series of acoustic pulses from the transducer array 12 and displaying signals representative of the magnitude of the echoes received from these pulses. Low voltage receive electronics 14 receive electrical signals form the transducer and process the signals to form images. A relatively high voltage transmit generator generates a relatively high-voltage electrical signals that are inputted to the transducer array 12 to be transduced to outgoing ultrasound. Transmit/Receive (T/R) high voltage switches 18 are provided that are switchable from one configuration, in which switches 18 electrically connect the transmit generator 16 to the transducer array 12 to input relatively high voltage electrical signals to the transducer array, to a second configuration, in which switches 18 electrically connect the transducer array 12 to the low-voltage receive electronics 14.

Image formation begins when T/R switches are placed in the first configuration to connect the transducer elements 12 to individual transmit circuits. Next, transmit generators 16 output time varying waveforms with delay and amplitude variations selected to produce a desired acoustic beam. Voltages of up to 200 Volts or more may be applied to the transducer elements 12. Once transmission is complete, the T/R high voltage switches 18 are switched to the second configuration to connect the transducer elements 12 to individual receive circuitry (in the low voltage receive electronics 14) associated with each element.

Note that the transducer array 12 shown in FIG. 1 has one common electrode 13, and the non-common electrodes may be multiplexed between high-voltage transmit and low-voltage receive signals. The conventional T/R high voltage switches 18 are the source of considerable expense and bulk in typical ultrasound systems. For modern, three-dimensional (3D) ultrasound systems, the channel count (and thus, the number of T/R high voltage switches required) can reach into the thousands making the bulk and expense of the high voltage switches impractical, if not prohibitive.

Ultrasonic transducers associated with ultrasound imaging systems may be driven from a single terminal with the second terminal grounded. A transducer may be used to transmit ultrasound signals as well as receive reflected ultrasound.

A signal received at a transducer (reflected signal) may typically be several orders of magnitude smaller than the signal (outgoing signal) that was transmitted due to, inter alia, signal attenuation by the target tissue. Some of the signal may be lost due to transducer inefficiencies as well. It may be thus necessary to couple the transducer to a high-voltage transmit signal while the ultrasound is being transmitted, and then to a sensitive low-noise preamplifier while the reflected ultrasound is being received.

A switch that couples the transducer to the transmit and receive signals must be capable of withstanding high peak transmit voltages (typically 50-200 volts) while isolating the preamplifier input from those voltage levels, since they would otherwise destroy the preamplifier. If a receiver for the signals from the transducers is fabricated as a high-density, low-voltage integrated circuit (IC), the switches themselves may need to be fabricated off-chip in a separate package from materials and devices that can withstand the high voltage transmit pulses.

Commercial ultrasound systems have been limited to one-dimensional (1-D) or linear transducer arrays until fairly recently. A typical number of transducers in such an array may be 128. Providing separate multiplex and receive circuitry is manageable with this many transducers, albeit with significant use of expensive high-voltage switches. Newer arrays, however, may be likely to be two-dimensional (2-D) or square arrays. The number of transducers in a two-dimensional array may range up to 128×128 or 16,384, and is often in the thousands. Maintaining separate receive, transmit, and multiplex partitioning for the transducers in such an array creates a tremendous burden in terms of cost, space, and complexity. The power consumption and heat dissipation of thousands of high-voltage multiplexers is enough to discourage the use of two-dimensional arrays in portable ultrasound imaging systems.

Accordingly, existing ultrasound systems with thousands of separate transmit and receive switches may be too expensive and/or too bulky for many applications. While a variety of systems and methods may be known, there remains a need for improved systems and methods.

SUMMARY OF THE INVENTION

A transducer drive according to the present invention may be incorporated in an ultrasonic imaging system convenient enough to be a common component of nearly every medical examination and procedure. An ultrasonic transducer drive according to the present invention provides the potential to have a broad and significant impact in healthcare. The present disclosure identifies various clinical applications of the present invention, but should not be limited thereto, as other applications will become attained as clinicians gain access to the system (employing the transducer drive) and method.

The preferred embodiments of the present invention may improve significantly upon existing methods and/or apparatuses. In particular, the present invention comprises an ultrasonic transducer drive that may be used in a hand held ultrasonic instrument such as one provided in a portable unit which performs B-mode or C-Mode imaging and collects three dimensional (3-D) image data. The preferred embodiments are particularly advantageous for C-Mode imaging with a planar (non-focused) transmit pulse, and is particularly useful when the transmit pulse is unfocused or minimally focused. The present invention is particularly advantageous when large numbers of transducer elements are driven together during transmit. For example a B-Mode or C-Mode system with plane wave transmit is particularly suited to obtaining the benefits of the present invention.

The present invention reduces the number of isolation elements that need to be provided in an ultrasound imaging system in that, instead of protecting the receive circuitry and low voltage system electronics from the transmit pulse transmitted by the relatively high voltage transmit circuit, the receive circuitry floats such that it "rides" the transmit pulse so that it never receives the voltage potential difference between the relatively high voltage transmit circuit and the system ground. This reduces the number of isolation elements that would otherwise be required in a system that protects the receive circuitry and low voltage system electronics from the transmit pulse. In particular, the present invention reduces the number of isolation elements (isolators) that have to withstand significant voltage drops. For example, switches at the transducer element/preamp interface never have to sustain significant voltage drops which is why they are easily integrated onto a low voltage integrated circuit (IC).

The transducer/transducer array at the channel preamp is connectable to the isolated ground. Separate switches in between the transducer/transducer array and between the transducer/transducer array and isolated ground can be provided to enable floating during transmit and then connection to the system ground when transmit is not occurring. Alternatively, a single switch can be provided between a transducer and the isolated ground (receiver ground). In this arrangement, during transmit the switch is on and the receiver input is shunted to ground. During receive the switch is open. In either case, the switches do not have to sustain significant voltage drops.

The isolated ground is connectable to the transmit signal driver circuit. In one embodiment a diode/resistor combination and a diode/field effect transistor (FET)/resistor (resistor optional) combination may be provided to achieve this connectability. Alternatively, FET/FET combinations could be substituted to do complete switching. Also, although a single FET is described in one embodiment for the connection between system ground and isolated ground, alternatively, a more complex switching network for a bipolar transmit signal could be substituted.

The isolation between the system electronics (low voltage system electronics) and receive circuitry is provided to carry signals in both directions to enable control of the receiver from the system.

In one aspect of the present invention, a floating transducer drive is provided that includes: a receive circuit electrically connected to an isolated local ground; a relatively high-voltage transmit circuit; a transducer; a system ground; a relatively low-voltage processing circuit; and isolation circuitry configured such that during a transmit event during which the relatively high voltage transmit circuit sends a relatively high voltage signal to the transducer, the isolated local ground is electrically connected to the transmit circuit; and wherein the isolation circuitry is configured such that when the transmit event is not occurring, the isolated local ground is electrically connected to the system ground.

In at least one embodiment, the isolation circuitry further includes an isolation circuit electrically connected between the receive circuit and the relatively low-voltage processing circuit In at least one embodiment, the isolation circuitry further comprises a transducer switch switchable from a receive position in which the transducer switch electrically connects the transducer to the receive circuit, to a transmit position in which the transducer switch electrically connects the transducer to the isolated local ground, wherein when the transducer switch is in the receive position, the isolated local ground is electrically connected to the system ground; and wherein, when the transducer switch in in the transmit position, the isolated local ground is electrically connected to the transmit circuit.

In at least one embodiment, the isolation circuit includes an isolation switch switchable from a ground position in which the isolation switch electrically connects the isolated local ground to the system ground, to a transmit position in which the isolation switch electrically connects the isolated local ground to the transmit circuit.

In at least one embodiment, the isolation switch disconnects the transmit circuit from the isolated local ground when in the ground position; and wherein the isolation switch disconnects the isolated local ground from the system ground when in the transmit position.

In at least one embodiment, the floating transducer drive further includes a relatively low value resistor electrically connecting the isolated local ground to the system ground.

In at least one embodiment, the floating transducer drive further includes a matching network electrically connecting the transmit circuit to the isolated local ground.

In at least one embodiment, the transducer comprises a plurality of transducers, and the transducer switch comprises a plurality of transducer switches at least equal to a number of the transducers.

In at least one embodiment, each of the isolation circuits comprises at least one isolation element comprising at least one of a resistor, a diode, a transformer, or an integrated circuit isolator.

In at least one embodiment, the isolation circuit comprises at least one isolation element that includes a component selected from the group consisting of: at least one resistor, at least one diode, at least one transformer, and at least one integrated circuit isolator.

In at least one embodiment, the receive circuit comprises a sample-and-hold connectable receivably to the transducer for sampling an incoming signal from the transducer and outputting an amplitude of the incoming signal.

In at least one embodiment, the receive circuit comprises an analog-to-digital converter connected receivably to the sample-and-hold for assigning a digital value to the amplitude and outputting the digital value.

In at least one embodiment, the receive circuit comprises a memory connected receivably to the analog-to-digital converter for storing the digital value and outputting the digital value.

In at least one embodiment, the receive circuit comprises an amplifier connectable receivably to the transducer for amplifying an incoming signal received from the transducer.

In at least one embodiment, the amplifier includes at least one filter for filtering the incoming signal.

In at least one embodiment, the receive circuit further comprises a pre-amplifier for amplifying the incoming signal and outputting an amplified incoming signal to the amplifier.

In at least one embodiment, the transducer is configured to convert a wave received to an incoming signal and to output the incoming signal to the receive circuit.

In at least one embodiment, the incoming signal is a signal selected from the group consisting of: an electro-magnetic signal; an electric signal; and an optical signal.

In another aspect of the present invention, a method of driving an ultrasound transducer is provided, the method including electrically connecting a relatively high voltage transmit circuit to the transducer; locally grounding a receive circuit via an isolated local ground; sending a relatively high voltage outgoing signal from the relatively high voltage transmit circuit to the transducer; transducing the outgoing signal to outgoing waves; receiving at least a portion of the outgoing waves as reflected waves reflected back to the transducer; transducing the reflected waves to an incoming signal; inputting the incoming signal to the receive circuit; converting the incoming signal by the receive circuit to a digital signal; outputting the digital signal to an isolation circuit; and outputting a relatively low voltage, isolated signal to a relatively low-voltage processing circuit.

In at least one embodiment, the method further includes connecting the isolated local ground to a relatively high voltage transmit circuit during performance of the sending a relatively high voltage outgoing signal from the relatively high voltage transmit circuit to the transducer, wherein the high voltage outgoing signal is carried to the transducer via the isolated local ground.

In at least one embodiment, the method further includes connecting the isolated local ground to a system ground during performance of the inputting the incoming signal to the receive circuit.

In at least one embodiment, a relatively low value resistor electrically connects the isolated local ground to a system ground.

In at least one embodiment, the method further includes a matching network electrically connects the transmit circuit to the isolated local ground.

In at least one embodiment, the matching network electrically connects the transmit circuit to the system ground via the relatively low value resistor.

In another aspect of the present invention, a sub-system for controlling switching between transmit and receive operations in an ultrasound imaging system is provided, the sub-system comprising: a relatively high voltage transmit circuit; a receive circuit electrically connected to an isolated local ground; a transducer configured to transduce an outgoing signal received from the relatively high voltage transmit circuit to outgoing ultrasound and to transduce incoming ultrasound reflected back to the transducer to an incoming signal and to output the incoming signal to the receive circuit; a sub-system isolated ground; a transducer switch switchable from a receive position in which the transducer switch electrically connects the transducer to the receive circuit, to a transmit position in which the transducer switch electrically connects the transducer to the isolated ground; a relatively low-voltage processing circuit; and an isolation circuit electrically connected between the receive circuit and the relatively low-voltage processing circuit; wherein, when the transducer switch is in the receive position, the isolated local ground is electrically connected to the system ground; and wherein, when the transducer switch in in the transmit position, the isolated local ground is electrically connected to the transmit circuit.

In another aspect of the present invention, an ultrasonic imaging system is provided, comprising: a system ground; a transducer; a receive circuit operatively connected to the transducer; a transmit circuit operatively connectable to the transducer; and a host computer operatively connected to the receive circuit, wherein the receive circuit floats when the transmit circuit sends a transmit pulse to the transducer, such that the receive circuit avoids receiving a voltage potential difference between the relative high voltage transmit circuit and the system ground.

In at least one embodiment, the system further includes: a transducer switch switchable from a receive position in which the transducer switch electrically connects the transducer to the receive circuit, to a transmit position in which the transducer switch electrically connects the transducer to the transmit circuit; a relatively low-voltage processing circuit; and an isolation circuit electrically connected between the receive circuit and the relatively low-voltage processing circuit; wherein, when the transducer switch is in the receive position, the isolated local ground is electrically connected to the system ground; and wherein, when the transducer switch in in the transmit position, the isolated local ground is electrically connected to the transmit circuit.

These and other features of the invention will become apparent to those persons skilled in the art upon reading the details of the floating transducer drive, systems, sub-systems and methods as more fully described below.

BRIEF DESCRIPTION OF THE DRAWINGS

FIG. 4A is a schematic diagram of a circuit that may be included in isolation circuitry according to an embodiment of the present invention.

FIG. 4B is a schematic diagram of a circuit that may be included in isolation circuitry according to another embodiment of the present invention

DETAILED DESCRIPTION OF THE INVENTION

Figure 1:
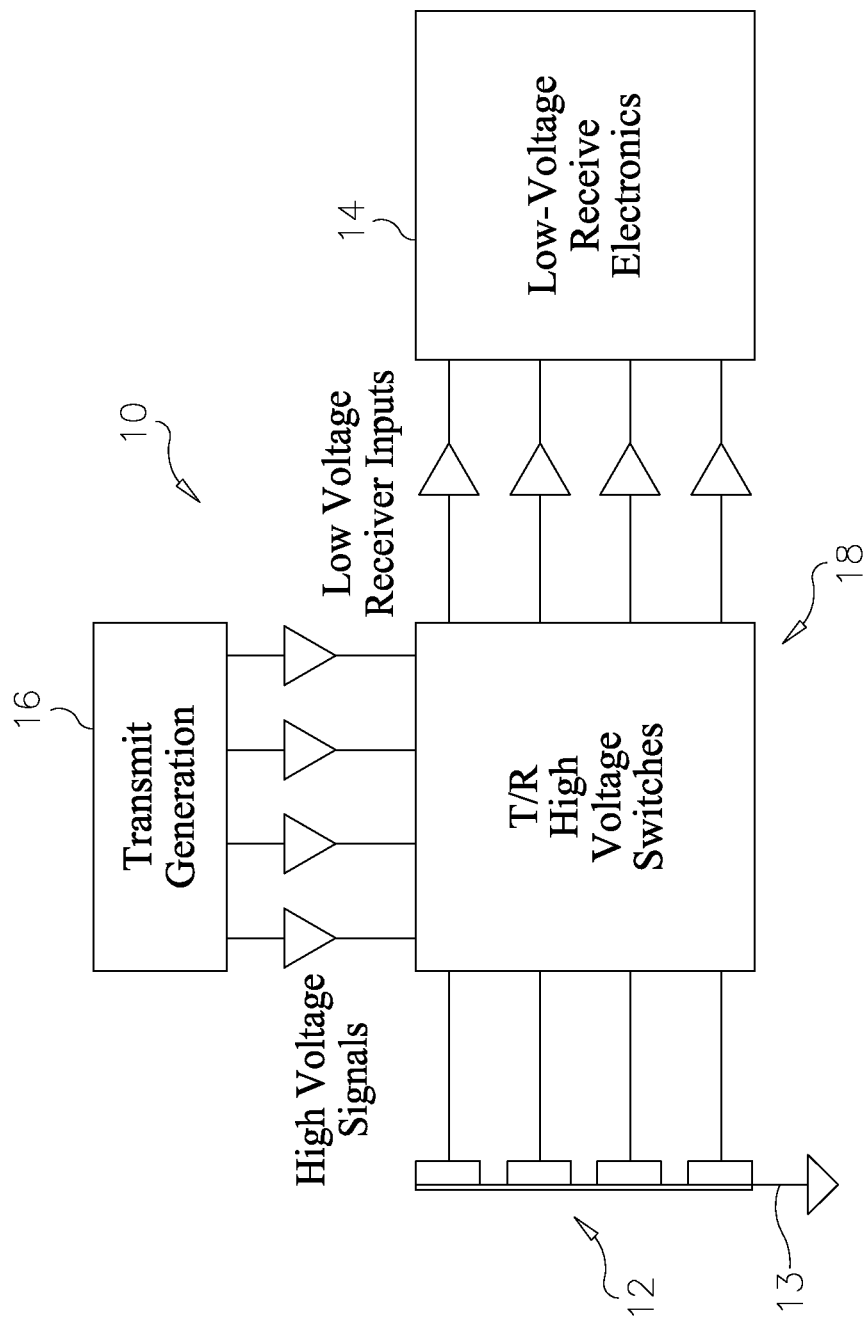
FIG. 1 is a schematic diagram of a conventional transducer drive.

Before the present floating transducer drive, systems, subsystems and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a transducer" or "a transducer element" includes a plurality of such transducers or transducer elements, respectively, and reference to "the signal" includes reference to one or more signals and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The present invention may be utilized with various products and services as discussed below, but is not limited thereto. The transducer drive and method for driving an ultrasound transducer may enable substantially fully integrated interfacing between high density 2-D transducer arrays and receive circuits fabricated as integrated circuits (IC) without individual high voltage switches on each input channel. It is noted that "channel" refers to an individual transducer and it associated front end electronics In at least one embodiment a receive circuit is provided as a floating device. Isolation circuitry receives output from the floating receive circuit. Because the number of channels interconnecting the transducer array and the floating receive circuit is much greater than the number connections to the isolation circuitry (i.e., the number of electrodes 124 is much greater than the number of connections 142) for outputting signals from the floating receive circuit to the isolation circuitry, a great reduction in the number of isolation devices required results in the present invention, relative to the large number of high voltage T/R switches 18 required in the conventional art. Also, because the signals outputted to the isolation circuitry are digital signals and not low noise, low amplitude transducer signals the isolation elements that are used in the isolation circuitry according to the present invention can be much simpler and much less costly than the high voltage T/R switches 18 of the conventional art.

Technicians may attempt to insert needles into a vein based on the surface visibility of the vein coupled with their knowledge of anatomy. While this approach works quite well in thin, healthy individuals, it can prove extremely difficult in patients who may be ill or obese. It may be desirable to have a relatively small, inexpensive, and portable ultrasound imaging system for guiding the insertion of intravenous (IV) devices like needles and catheters into veins, or for drawing blood.

Manual palpation is an exceedingly common diagnostic procedure. Clinicians use their sense of touch to feel for subcutaneous lumps or even to estimate the size of lymph nodes or other masses. While palpation undoubtedly yields valuable qualitative information, numerous studies have shown it to have extremely poor sensitivity and that quantitative size estimates may be completely unreliable. It may be desirable to have a relatively small, inexpensive, and portable ultrasound imaging system to aid in observing subcutaneous tissues.

Ultrasound may be used to search for internal defects in metallic or ceramic parts in a broad variety of industrial applications. Current systems may be cost effective, but may be unwieldy and acquire limited data, making it difficult to ensure that a thorough search has been performed. It may be desirable to have a relatively small, inexpensive, and portable ultrasound imaging system to aid in non-destructive evaluation.

Furthermore, new users may expect ultrasound images to produce representations parallel to the skin's surface, i.e. C-Scan images. It would be desirable for a low cost, system to be capable of producing C-Scan images. It may further be desirable to display data in the intuitive C-scan format to allow clinicians with little or no training in reviewing ultrasound images to make use of the device.

Ultrasound imaging devices may be too expensive for some applications. It may be desirable for a beamformer to be fabricated using large scale integration to enable the system to be produced at a lower cost.

Ultrasound imaging devices may be insufficiently portable for some applications. It may be desirable for an ultrasonic imaging device to be of a small size to make it easy to carry the device in a pocket or on a belt attachment. This may make the device as convenient as a stethoscope and will thus open new applications. It may be desirable for a beamformer to be fabricated using large scale integration to enable the system to be portable.

Figure 2:
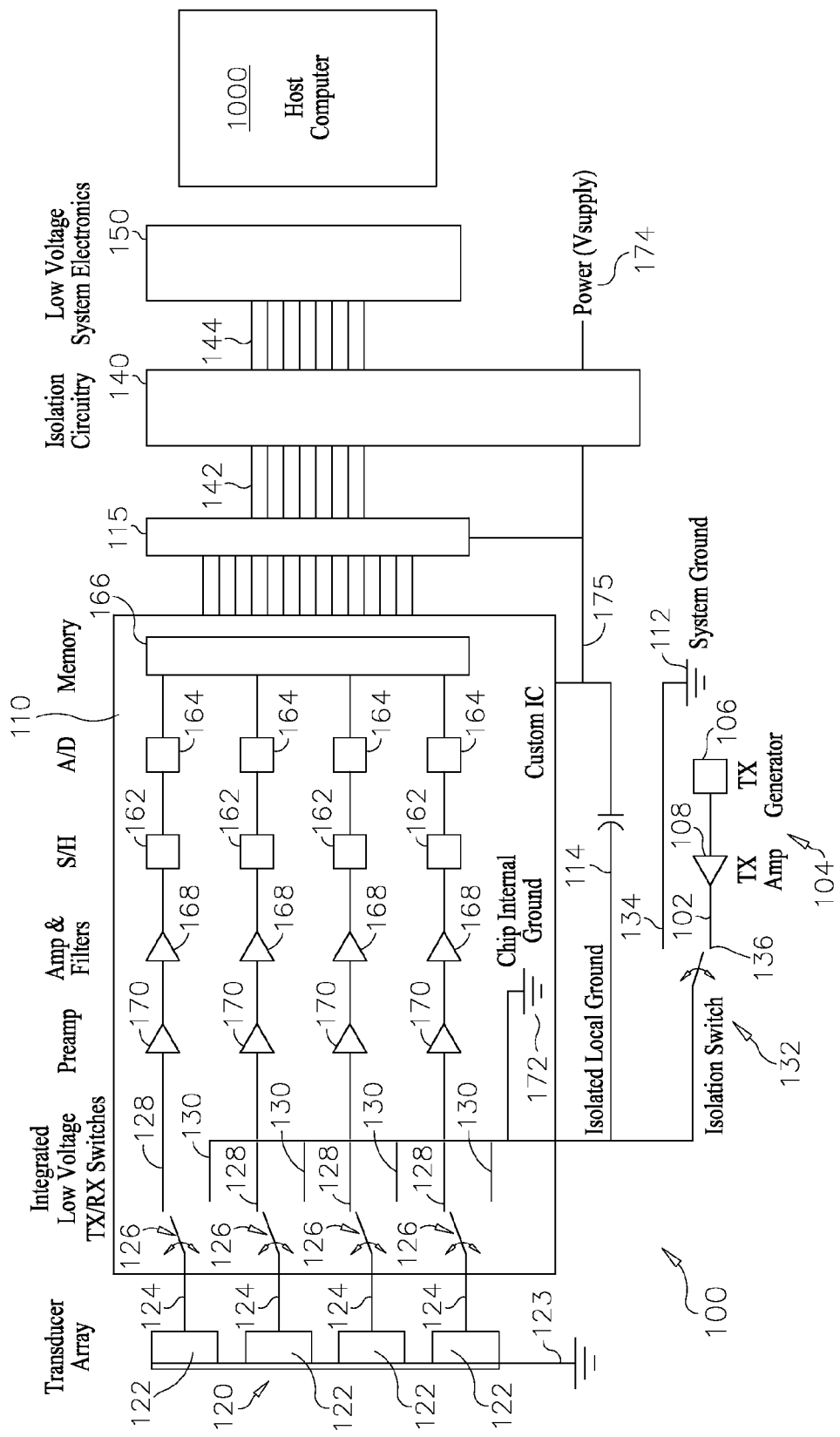
FIG. 2 is a schematic diagram of a transducer drive according to an embodiment of the present invention.

FIG. 2 shows a floating transducer drive system 100 that may be used in an ultrasonic imaging system, for example, according to an embodiment of the invention. Floating transducer drive 100 may be used in a relatively small, inexpensive, and portable ultrasound imaging system 200 such as that shown in FIG. 5. A common transmit pulse 102 such as used in current C-mode ultrasonic imaging systems is provided by a relatively high voltage transmit circuit 104 which may include a transmit signal generator 106 and a transmit signal amplifier 108 as illustrated in FIG. 2.

A receive circuit 110 is allowed to float with respect to the system ground 112 in a manner as described below. Receive circuit 110 is electrically connected to an isolated local ground 114. As shown in FIG. 2, receive circuit 110 is formed as a custom integrated circuit (IC). Alternatively, the same or substantially similar functionality may be provided by a combination of integrated circuit chips and other board level electronics connected to isolated local ground 114 and otherwise connected in the same manner as the custom IC shown to perform as described hereafter. It should be clear to one of ordinary skill in the art that the floating receive circuit 110 may include several additional components to interface and provide signals to the custom integrated circuit.

Transducer/transducer array 120 is provided with one or more transducers 122 (typically, many more than one, as described above). In one preferred embodiment, transducer array has six thousand transducers 122, although this number may be greater or fewer, and may vary widely depending upon the specific application that the transducer is designed to image. The transducer array 120 includes one common electrode 123 that connects all transducer elements 122 in the array 120 to ground, and each transducer element 122 has a second, non-common electrode 124 of its own that is not common with any other transducer element 122. Non-common electrodes 124 are each individually connected to a respective transducer switch 126 that is switchable from a receive position in which the transducer switch electrically connects 128 the transducer element 122 to the receive circuit 110, to a transmit position in which the transducer switch 122 electrically connects 130 the transducer element 122 to the transmit circuit 104. The transducer switches 126 are shown in the receive position in FIG. 2.

An isolation switch 132 is provided that is switchable from a ground position 134 in which the isolation switch 132 electrically connects the isolated local ground 114 to the system ground 112, to a transmit position 136 in which the isolation switch 132 electrically connects the isolated local ground 114 to the transmit circuit 104. In this configuration, the transducer currents are conducted from the transmit circuit via the isolated local ground so the local ground net should be designed to accommodate the currents and minimize voltage drop. Isolation switch 132 is shown in the transmit position in FIG. 2. The isolation switch 132 disconnects the transmit circuit 104 from the isolated local ground when the isolation switch 132 is in the ground position. The isolation switch 132 disconnects the isolated local ground 114 from the system ground 112 when the isolation switch is in the transmit position.

Figure 3:
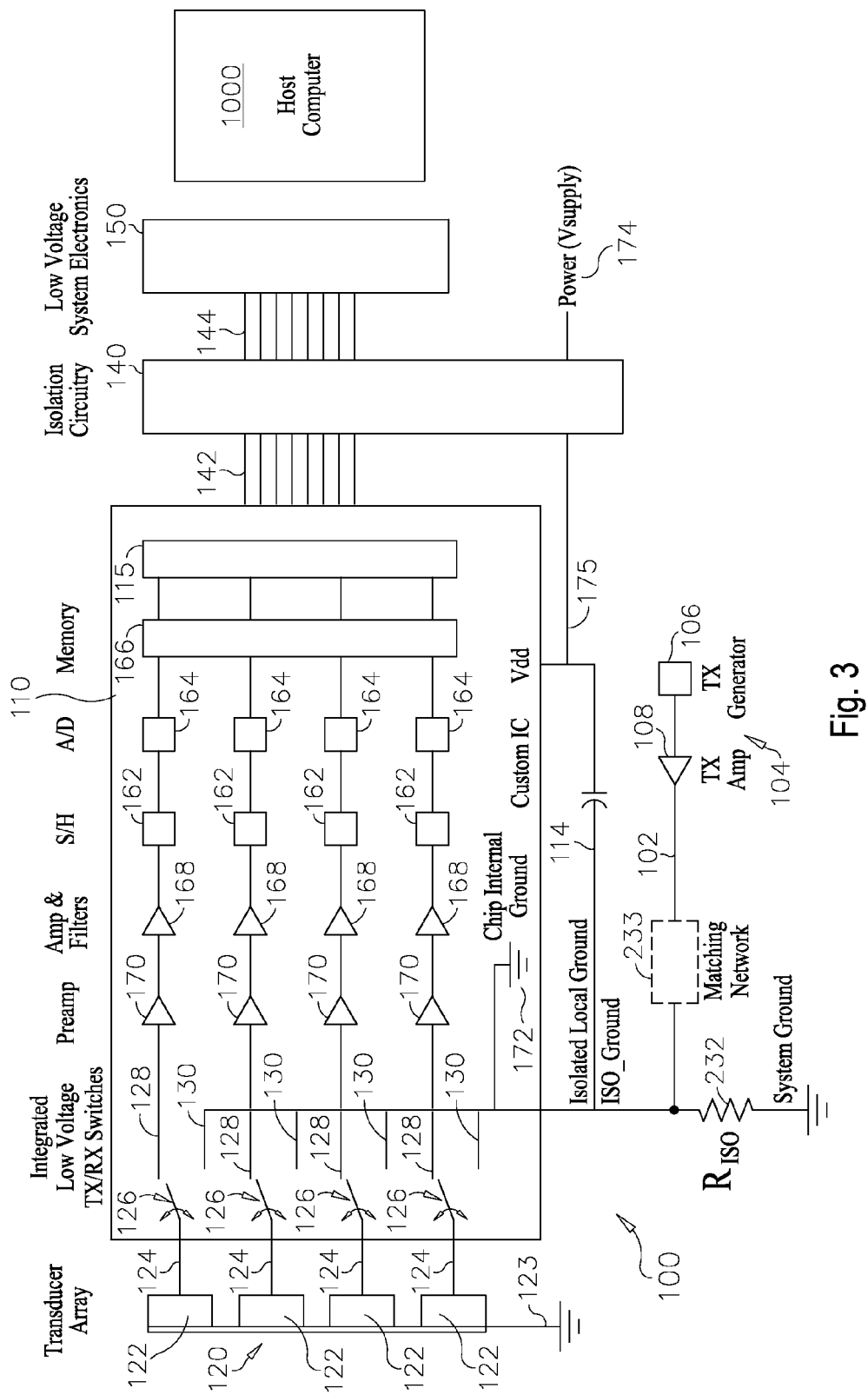
FIG. 3 is a schematic diagram of a transducer drive according to another embodiment of the invention.

Isolation circuitry 140 is electrically connected between the receive circuit 110 and a relatively low-voltage system electronics 150, and between (one or more) power source(s) (Vsupply) 174 and isolated power(s) (ISO_Vsupply) 175. It should be noted here that the receive circuitry 110 is also relatively low voltage, as receive circuitry 110 also floats relative to the relatively high voltage transmit circuit 104 potentials. The receive circuitry 110 reaches high voltage levels relative to the system ground, but the receive circuitry 110 never experiences high voltages with respect to its internal reference, the isolated local ground. For example, voltage differences in the relatively high voltage circuitry may be in the range of about five to about 200 volts, while voltage differences in the receive circuitry will typically be in the range of about one to about five volts and the system electronics 150 supply voltage 174 will typically be in the range of about one to about five volts. The system electronics 150 provide a data and signaling path between the isolated receive circuits and a host computer 1000. The host computer 1000 can be connected to the system via hard wire connection, wireless connection, either locally or over a wide area network such as the Internet, via a custom interface, USB connection, Ethernet, etc. The host computer 1000 may be a separate computer or an embedded computer. In one preferred embodiment, the host computer 1000 comprises an embedded computer running on the LINUX operating system and the embedded computer 1000 is connected via USB and is in the same case as the subsystem 100, including the transducer 120 and other components shown in FIG. 2. In this type of embodiment, the system 2000 is completely untethered since the embedded computer 1000 and CPU 1002 are small and contained with an integrated system 2000, such that the entire encased system 2000 is about the size of a television remote controller. Connections 142 electrically connect receive circuit 110 with isolation circuitry 140 for outputting digital signals from the receive circuit to the isolation circuitry. Connections 144 electrically connect the isolation circuitry 140 to the low voltage system electronics 150 to output isolated, relatively low voltage digital signals to the low voltage (typically in the range of about 1 to 5 volts) system electronics 150. Isolation circuitry 140 also passes control and data signals from low voltage electronics 150 to receive circuitry 110. In other words, data moves in both directions. Typically, the interface data rate from 110 to 150 (upstream) is much higher than the downstream data rate from 150 to 110. Also included in receive circuitry 110 is control circuitry 115. Control circuitry 115 maintains front-end bias and configuration settings of the subsystem 100 and provides signals to control sampling, data readout and other interface requirements. Control circuitry may be located separated from the receive circuitry IC 110 as shown in FIG. 2 (off chip), or may be integrated on the IC 110 as shown in FIG. 3 (on chip), or may be provided as a combination of off chip and on chip components. Further optionally, control circuitry may be integrated with another component such as memory 166.

When the transducer switches 126 are in the receive positions 128, control of the isolation switch 132 ensures that the isolation switch 132 is in position 134, so that the isolated local ground 114 is electrically connected to the system ground 112. When the transducer switches 126 are in the transmit positions 130, control of the isolation switch 132 ensures that the isolation switch is in position 136, so that the isolated local ground 114 is electrically connected to the transmit circuit 104.

The receive circuit 110 acquires and digitizes the signals from each channel (one channel per transducer element 122) and then sends the digitized signals over a typical digital bus (connections 142) to the isolation circuit 140 and then to the system electronics 150. Thus, there may be several thousand channels (where several thousand transducers 122 are in array 120), but digitization by the receive circuit 110 configures the input from the channels such that the number of isolation signals required is that number required to transmit digital data. For example, for a system having a transducer array 120 with a number of transducers 122 in the range of about four thousand to about ten thousand, the number of connections 142 (equal to the number of connections 144) is in the range of about two to about one hundred, more typically about ten to about forty. In one preferred embodiment, the number of transducers 122 is six thousand, the number of channels is six thousand, and the number of connections 142 is eighteen.

Because the signals outputted to isolation circuitry 140 via connections 142 are digital signals and not low amplitude analog signals that are outputted by transducer elements at 124, the isolation elements can be much simpler and much less expensive than the high voltage T/R switches 18 (see FIG. 1) that are required to be used in the conventional art. For example, in one particular embodiment, isolation circuitry is limited to the components required for eighteen signals, where eighteen signals 142 are provided in the system and the transducer array 120 has six thousand transducers and therefore six thousand electrodes 124. It is noted that all of these numbers may vary depending upon the application, but in each embodiment, the number of isolation elements is much less than the number of transducers. Also, because the number of connections 142 is much less than the number of channels (electrodes 124) the number of isolation elements in the required in the isolation circuitry 140 of the present invention, is much less than the number of high voltage T/R switches 18 required in the conventional art shown in FIG. 1, in cases where both employ the same number of transducer elements.

In at least one embodiment, at least one isolation element includes at least one of a resistor, a diode, a transformer, or an integrated circuit isolator.

In at least one embodiment, at least one isolation element includes a component selected from the group consisting of: at least one resistor, at least one diode, at least one transformer, and at least one integrated circuit isolator.

Receive circuit 110 includes a sample-and-hold 162 connectable receivably to the transducer 120 for sampling an incoming signal from the transducer 120 and outputting an amplitude of the incoming signal. In the embodiment shown in FIG. 2, receive circuit 110 includes a plurality of sample-and-holds 162. In one preferred embodiment, there are eight sample and holds 162 and an equal number of memories 164 per transducer signal path 128. However, the number of sample and holds 162 and memories 164 may vary. Receive circuit 110 further includes an analog-to-digital (A/D) converter 164 connected receivably to sample-and-hold 162 for assigning a digital value to the amplitude and outputting the digital value. In the embodiment shown in FIG. 2, receive circuit 110 includes a plurality of A/D converters 164, the number of which may be equal to the number of sample-and-holds 162. Alternatively, a smaller number of A/D converters can be employed, the A/D converters being shared across several sample and holds 162 and/or channels.

Receive circuit 110 may further include a memory 166 connected receivably to the analog-to-digital converter(s) 164 for storing the digital value until it is read out via the isolation circuitry 140 by the system electronics 150. The memory 166 is typically a digital memory and can optionally be integrated with other elements of the receive channel or placed in a separate integrated circuit. It should be understood that the various elements in the receive channel paths can be contained on a single custom integrated circuit or those functions/elements can be distributed across multiple integrated circuits with a single floating receive circuit. Further optionally, multiple receive circuits 110 can be provided in a system 100 each connected to different subsets of the transducers 122 in the transducer array 120. In the embodiment shown in FIG. 2, memory 166 is connected receivably to all A/D converters 164 in receive circuit 110.

The receive circuit 110 may include an amplifier 168 connectable receivably to the transducer 120 for amplifying an incoming signal received from the transducer 120. Additionally, the amplifier 168 may include at least one filter for filtering the incoming signal. Preferably a bandpass filter is used to reduce noise outside the bandwidth of the transducer 122. Further additionally, the receive circuit 110 may include a pre-amplifier 170 for amplifying the incoming signal from the transducer and outputting an amplified incoming signal to the amplifier 168. In the embodiment of FIG. 2, the receive circuit 110 is provided with a plurality of amplifiers 168 each having at least one filter and a plurality of preamplifiers 170, wherein the number of preamplifiers 170 is equal to the number of amplifiers 168 and the number of amplifiers is equal to the number of transducer elements 122.

The receive circuit 110 may be provided with an internal ground 172 as shown in FIG. 2. A power source 174 is also electrically connected to the floating transducer drive to provide electrical power to it.

FIG. 3 shows a floating transducer drive system 100 that may be used in an ultrasonic imaging system, for example, according to another embodiment of the invention. Floating transducer drive 100 may be used in a relatively small, inexpensive, and portable ultrasound imaging system 200 such as that shown in FIG. 5. A common transmit pulse 102 such as may be used in a C-mode ultrasonic imaging system is provided by a relatively high voltage transmit circuit 104 which may include a transmit signal generator 106 and a transmit signal amplifier 108 as illustrated in FIG. 3. Transmit voltage levels are typically levels in a range from about 5 V to about 200 V, more typically in a range from about 5 V to about 100 V.

A receive circuit 110 is allowed to float with respect to the system ground 112 in a manner as described below. Receive circuit 110 is electrically connected to an isolated local ground 114. As shown in FIG. 3, receive circuit 110 is formed as a custom integrated circuit (IC). Alternatively, the same or substantially similar functionality may be provided by a combination of integrated circuit chips and other board level electronics connected to isolated local ground 114 and otherwise connected in the same manner as the custom IC shown to perform as described hereafter. It should be understood that there is control circuitry included within the receive circuitry 110 that may be as simple as a digital state machine or more complex such as a microcontroller.

Transducer/transducer array 120 is provided with one or more transducers 122 (typically, many more than one, as described above). The transducer array 120 includes one common electrode 123 that connects to all transducer elements 122 in the array 120 to ground, and each transducer element 122 has a second, non-common electrode 124 of its own that is not common with any other transducer element 122. Non-common electrodes 124 are each individually connected to a respective transducer switch 126 that is switchable from a receive position in which the transducer switch electrically connects 128 the transducer element 122 to the receive circuit 110, to a transmit position in which the transducer switch 122 electrically connects 130 the transducer element 122 to the transmit circuit 104. The transducer switches 126 are shown in the receive position in FIG. 3.

Although the embodiments of FIGS. 2 and 3 show the transducer array 122 provided with a plurality of transducers 122, with each transducer connectable to receive circuitry 110 via a dedicated electrode 124, respectively, alternatively, transducer array 122 may be configured with a plurality of transducers 122 formed as subarrays, wherein each subarray is a subset of the array and the total number of subarrays makes up the array. In this embodiment, a common electrode 124 may be electrically connected to each subarray of transducers, respectively, rather than connecting a dedicated electrode to each individual transducer 122.

A relatively low value resistor 232 may be electrically connected in series to the system ground 112, with the isolated local ground 114 and transmit signal circuit 104 connected in parallel to the relatively low valued resistor 232. As shown, the relatively low value resistor 232 has a value of about ten ohms, but the value of the relatively low value resistor 232 may have other values, as can be selected to perform its function relative to the impedance of the transducer array 120, for example. If the resistance value of 232 is large relative to the impedance of the transducer 120 at the transmit frequency, the isolated local ground is driven to the transmit voltage by the transmit amplifier 108. Thus, the value of 232 needs to be large compared to the transducer 120 impedance, but at the same time, small enough to provide minimal voltage drop for the DC current path between the isolated local ground 114 and the system ground 112. For example, if a large area transducer (transducer 120) has a center frequency impedance of two ohms, and the average DC current path between 114 and 112 is one mA, a resistor 232 having a five ohms resistance value would add minimal load to the transmit amplifier 108 and still only cause a five mV DC voltage drop. Optionally, a matching network can be introduced between the transmit amplifier 108 and the transducer 120 to compensate for the complex impedance of the transducer 120. FIG. 3 shows an optional matching network 233 connected in series with transmit signal circuit 102 and connected to system ground 112, as well as isolated local ground 114. Isolation circuitry 140 is electrically connected between the receive circuit 110 and relatively low-voltage system electronics 150, and between power source (Vsupply) 174 and isolated power (ISO_Vsupply) 175. Connections 142 electrically connect receive circuit 110 with isolation circuitry 140 for outputting digital signals from the receive circuit to the isolation circuitry. Connections 144 electrically connect the isolation circuitry 140 to the low voltage system electronics 150 to output isolated, relatively low voltage digital signals to the low voltage system electronics 150. Like the embodiment of FIG. 2 and all other embodiments, incoming control and data signals also pass in the opposite direction, from low voltage system electronics 150 through isolation circuitry 140 to receive circuitry 110.

When the transducer switches 126 are in the receive positions 128, the isolated local ground 114 is electrically connected to the system ground 112. When the transducer switches 126 are in the transmit positions 130, the isolated local ground 114 is electrically connected to the transmit circuit 104.

The receive circuit 110 acquires and digitizes the signals from each channel (one channel per transducer element 122) and then sends the digitized signals over a digital bus (connections 142) to the isolation circuit 140 and then to the system electronics 150. Control signals and data are also sent from the system electronics 150 through the connections 144, isolation circuitry 140 and connections 142 to receive circuitry 110. Thus, there may be several thousand channels (where several thousand transducers 122 are in array 120), but digitization by the receive circuit 110 configures the input from the channels such that the number of isolation signals required is that number required to transmit digital data.

Because the signals outputted to isolation circuitry 140 via connections 142 are digital signals and not low amplitude analog signals that are outputted by transducer elements at 124, the isolation elements can be much simpler and much less expensive than the high voltage T/R switches 18 (see FIG. 1) that are required to be used in the conventional art. Also, because the number of connections 142 is much less than the number of electrodes 124 the number of isolation elements in the required in the isolation circuitry 140 of the present invention, is much less than the number of high voltage T/R switches 18 required in the conventional art shown in FIG. 1, in cases where both employ the same number of transducer elements.

In at least one embodiment, at least one isolation element includes at least one of a resistor, a diode, a transformer, or an integrated circuit isolator.

In at least one embodiment, at least one isolation element includes a component selected from the group consisting of: at least one resistor, at least one diode, at least one transformer, and at least one integrated circuit isolator.

Receive circuit 110 includes a sample-and-hold 162 connectable receivably to the transducer 120 for sampling an incoming signal from the transducer 120 and outputting an amplitude of the incoming signal. In the embodiment shown in FIG. 2, receive circuit 110 includes a plurality of sample-and-holds 162, the number of which is at least equal to the number of transducer elements 122. Receive circuit 110 further includes an analog-to-digital (A/D) converter 164 connected receivably to sample-and-hold 162 for assigning a digital value to the amplitude and outputting the digital value. In the embodiment shown in FIG. 3, receive circuit 110 includes a plurality of A/D converters 164, the number of which may be equal to the number of sample-and-holds 162. Alternatively, a smaller number of A/D converters can be employed, the A/D converters being shared across several sample and holds 162 and/or channels (circuitry associated with each transducer element).

Receive circuit 110 may further include a memory 166 connected receivably to the analog-to-digital converter(s) 164 for storing the digital value until it is read out via the isolation circuitry 140 by the system electronics 150. The memory 166 is typically a digital memory and can optionally be integrated with other elements of the receive channel or placed in a separate integrated circuit. It should be understood that the various elements in the receive channel paths can be contained on a single custom integrated circuit or those functions/elements can be distributed across multiple integrated circuits with a single floating receive circuit. Further optionally, multiple receive circuits 110 can be provided in a system 100 each connected to different subsets of the transducers 122 in the transducer array 120. In the embodiment shown in FIG. 3, memory 166 is connected receivably to all A/D converters 164 in receive circuit 110.

The receive circuit 110 may include an amplifier 168 connectable receivably to the transducer 120 for amplifying an incoming signal received from the transducer 120. Additionally, the amplifier 168 may include at least one filter for filtering the incoming signal. Further additionally, the receive circuit 110 may include a pre-amplifier 170 for amplifying the incoming signal from the transducer and outputting an amplified incoming signal to the amplifier 168. In the embodiment of FIG. 3, the receive circuit 110 is provided with a plurality of amplifiers 168 each having at least one filter and a plurality of preamplifiers 170, wherein the number of preamplifiers 170 is equal to the number of amplifiers 168 and the number of amplifiers is equal to the number of transducer elements 122.

The receive circuit 110 may be provided with an internal ground 172 as shown in FIG. 3. A power source 174 is also electrically connected to the floating transducer drive to provide electrical power to it.

Figure 5:
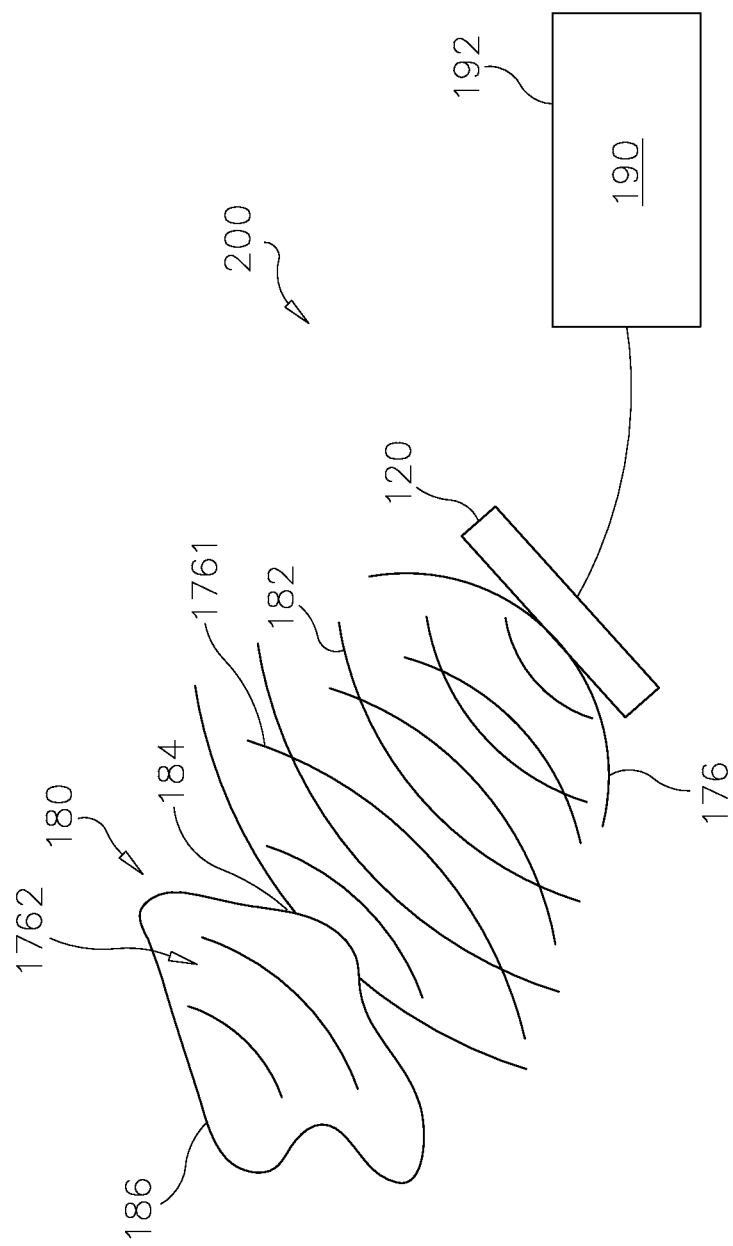
FIG. 5 is a schematic diagram of an ultrasonic imaging system employing a floating transducer drive according to an embodiment of the present invention.

Transducer 120 is configured to convert a wave received (e.g., see FIG. 5 number 176 to an incoming signal(s) and to output the incoming signal(s) to the receive circuit 110 via terminal(s) 124. As shown in the embodiments of FIGS. 2 and 3, the incoming signal is an electrical signal, having been converted from an incoming acoustic wave by the transducer.

Additionally or alternatively, the incoming signal could include an electro-magnetic signal and/or an optical signal.

Likewise, the outgoing signal (common transmit pulse) 102 may be an electrical signal, an electromagnetic signal, and/or an optical signal, but the preferred embodiment, where the outgoing signal is an electrical signal, is described here. The outgoing transmit signal is converted to an acoustic wave by the transducer.

In a preferred embodiment, the transmit signal is a four-cycle, 5 MHz tone burst that is generated by a high voltage switching network. Initially the transmit signal is formed as a square wave, and the matching network (if provided) and transducer impedance act to filter the square wave to a wave approximating a four-cycle sine wave. Most of the filtering is achieved by the narrow band characteristic of the transducers 122.

In at least one embodiment, the transmit signal generator 106 may be a storage device, such as a read-only memory (ROM), an oscillator such as a crystal oscillator, a resonant circuit such as a resistor-inductor-capacitor (RLC) or tank circuit, a resonant cavity such as a ruby laser or a laser diode or a tapped delay line.

In the event that transmit signal generator 106 is a storage device, outgoing signal 102 may have been stored previously, to be read out when needed. In this embodiment, several versions of outgoing signal 102 may be stored for use with various target objects 180 (see FIG. 5) to be imaged. Floating transducer drive 100 may thus be set to produce a signal appropriate for a particular object 180 to be imaged by choosing one of the stored versions of outgoing signal 102.

In the event that transmit signal generator 106 is an oscillator, outgoing signal 102 may be a sinusoid of varying frequencies. In this case, outgoing signal 102 may be generated at an arbitrarily high clock speed and still be forced through filters of arbitrarily small bandwidth. This may be advantageous, for example, if a wide band signal is inconvenient. A resonant circuit or a resonant cavity may work in a similar manner. Furthermore, an oscillator may be used to produce a range of frequencies, from which a frequency that generates an optimum response may be selected.

In the event that transmit signal generator 106 is a tapped delay line, outgoing signal 102 could be generated in a manner similar to a spreading code in a code division multiple access (CDMA) format cell phone system. In this case outgoing signal 102 would not need to be a pure sinusoid, but may be a code with a fixed repetition length, such as a Walsh or a Gold code. This may, for example, allow an autocorrelation length of outgoing signal 102 to be adjusted to enhance or suppress coded excitation of an incoming signal.

If transmit signal generator 106 is a tapped delay line it may be followed by an equalizer to bias or pre-emphasize a range of frequencies in outgoing signal 102. In one embodiment, the equalizer may be an adaptive equalizer that operates on an incoming signal analogous to the sound reflected by the imaged object 180. In this case, the incoming signal could be measured and the result applied to the adaptive equalizer to compensate for frequency attenuation of the sound by amplifying one or more frequencies of the incoming signal or outgoing signal 102 as necessary. This may be useful if, for example, object 180 attenuates or absorbs sound to the point that no return signal is available for imaging. In one embodiment, the adaptive equalizer could be placed in parallel with transmit signal generator 106 and in series with the incoming signal.

In at least one embodiment, an equalizer can be placed in series with transmit signal generator 106. In this case the equalizer can emphasize a particular frequency or frequencies in outgoing signal 102. The equalizer may, for example, place a bias or pre-emphasis toward lower frequencies on outgoing signal 102. This embodiment may be appropriate if, for example, object 180 to be imaged is expected to have features that attenuate lower frequencies significantly more than higher frequencies to the extent that imaging may be difficult. The converse may be true as well, in that the equalizer may have a bias or pre-emphasis toward higher frequencies.

As noted above, the transmit circuit 104 may include an amplifier 108. Amplifier 108 may be a generator amplifier for amplifying the outgoing signal 102. Generator amplifier 108 may pre-emphasize certain frequencies of outgoing signal 102 to suit the attenuation characteristics of object 180 to be imaged as well. The transmit signal generator 106 may also include an oscillator to produce an appropriate modulation frequency, such as a radio frequency (RF) signal, with which to modulate outgoing signal 102.

Transducer 120 may be provided for converting outgoing signal 102 to outgoing ultrasound 182 (See FIG. 5) at a frequency of outgoing signal 102. Transducer 120/transducer element 122 may be a piezoelectric element, a voice coil, a crystal oscillator, a sono-luminescent transducer, or a Hall effect transducer. In one embodiment, reversals of outgoing signal 102 produce vibration of a surface of transducer element 122 at substantially the frequency of outgoing signal 102. In another embodiment, reversals of outgoing signal 102 produce vibrations of a surface of transducer element 122 at frequencies that are significantly higher or lower than the frequency of outgoing signal 102, such as harmonics of outgoing signal 102. This vibration may, in turn, produce successive compressions and rarefactions of an atmosphere surrounding the surface of transducer 120/transducer element 122, also at substantially the frequency of outgoing signal 102. If the frequency of outgoing signal 102 is substantially higher than a frequency at which sound may be heard, the successive compressions and rarefactions of the atmosphere may be termed ultrasound.

Each of transducer switches 126 and isolation switch 132 may be an electronic switch, a micro-mechanical switch, a transistor, a field-effect transistor (FET), a bi-polar transistor, a metal-oxide-semiconductor (MOS) transistor, a complementary metal-oxide-semiconductor (CMOS) transistor, a metal-oxide-semiconductor field-effect transistor (MOSFET), or a clamp diode.

If outgoing ultrasound 182 is reflected by object 180, some of outgoing ultrasound 182 may return to ultrasound imaging system 200 as reflected ultrasound 176, see FIG. 5. In at least one embodiment, outgoing ultrasound 182 may be delayed or attenuated partially by object 180. A first reflected portion 1761 of outgoing ultrasound 182, for example, may be reflected immediately upon encountering a nearer surface 184 of object 180 while a second reflected portion 1762 of outgoing ultrasound 182 is not reflected until it encounters a further surface 186 of object 180. A round trip of second portion 1762 will thus be longer than a round trip of first portion 1761, resulting in a delay of second portion 1762 relative to first portion 1761, as well as delays of both first and second portions 1761, 1762 relative to outgoing ultrasound 182. Furthermore, second portion 1762 may be damped or attenuated by a material of object 180. The delays may be measured for disparate points of object 180, producing an image 190 of object 180 which can be displayed on a display 192.

In at least one embodiment, transducer 120 may convert at least a portion of reflected ultrasound 176 to an incoming signal outputted to receive circuit 110 via channel/electrode 124. In at least one embodiment, the incoming signal may be an electro-magnetic signal, an electrical signal, or an optical signal.

In at least one embodiment, memory 166 may comprise a register for storing incoming signal received from the A/D converter(s) 164. In at least one embodiment, receive circuit may include a digital signal processor (not shown) for processing incoming signals. In another embodiment, components other than the analog components between the transducer array 120 and the memory 166 of receive circuit 110 may be implemented in software on a microprocessor. In at least one embodiment, as noted above, any or all of the components of receive circuit 110 may be implemented in a plurality of integrated circuits, rather than a single readout IC. Implementation of receive circuit 110 as an IC or in software may reduce system size and complexity.

FIG. 4A is a schematic representation of a circuit that may be included in isolation circuitry 140 according to an embodiment of the present invention for isolating a DC power supply signal. For a typical band-limited transmit signal, the isolation provided by the isolation circuitry can be in the form of an inductor 140-1. In this situation, while the power source 174 is not fully isolated in the traditional sense, it is isolated with a large impedance within the bandwidth of the transmit signal from the high voltage transmit circuit 104. During a transmit event, the ISO_GND signal is driven to the transmit voltage, so ISO_Vsupply floats and maintains a constant voltage with respect to ISO_GND. The inductor acts as a high impedance with respect to the transmit signal frequency, so the two supply voltages can move independently. The inductor 140-1 blocks the high-frequency content of the transmit pulse, but still allows DC energy flow into the isolated power supply 174. A capacitor 105 may be provided to supply energy to the isolated circuits during the brief transmit pulse. The capacitor 107 provided on the Vsupply 104 side filters disturbances that may be generated during transmit because the inductor impedance is still finite at the transmit frequency.

This approach takes advantage of the knowledge of the characteristics of the transmit signal and the fact that the transmit pulse is very narrow in time. The system ground 112 and isolated local ground (ISO_GND) 114 are only separated in voltage during the transmit event. They are at approximately the same voltage level whenever the transmit is not active, which is the majority of the time.

FIG. 4B is a schematic representation of a power supply isolation circuit that may be included in isolation circuitry 140 according to another embodiment of the present invention. For a unipolar transmit pulse, the ISO_GND 114 may only be driven with a positive voltage with respect to the system ground 112. In this situation, the inductor 140-1 can be replaced with a diode 140-2. The diode 140-2 is on and supplying power when transmit is not active. During transmit the ISO_GND 114 is driven positive with respect to the system ground 112 (providing energy to the transducer 120) and the diode 140-2 is off. Again, the capacitor 152 across ISO_Vsupply 174 and ISO_GND 114 provides energy to the isolated circuits during the brief transmit time.

Figure 4C:
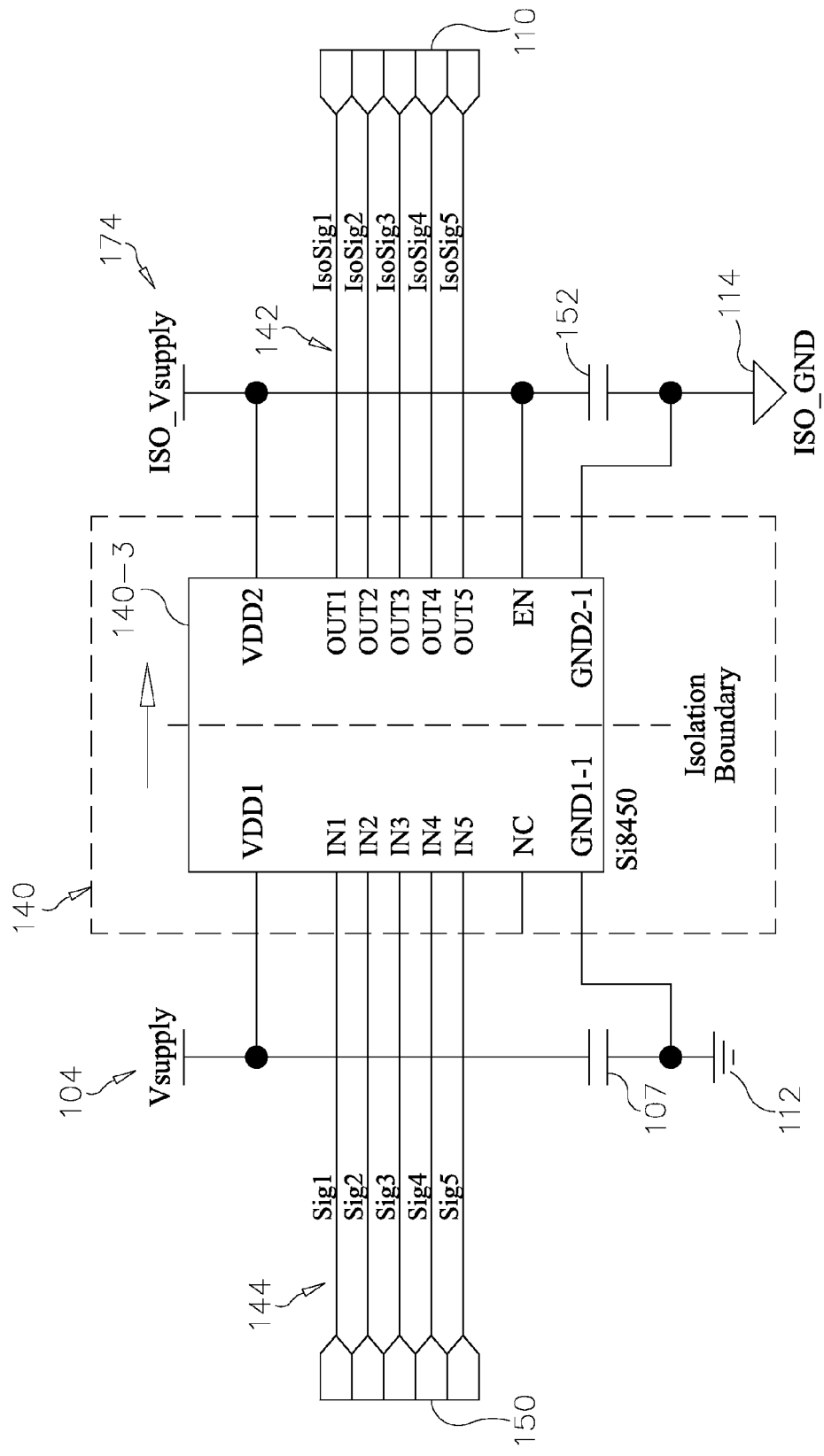
FIG. 4C is a schematic diagram of an integrated circuit that may be included in isolation circuitry according to an embodiment of the present invention.

FIG. 4C is a schematic representation of isolation circuitry that may be used in 140 according to another embodiment of the present invention. Integrated circuits provided on a chip 140-3 may be used for isolation of data signals between the receiving circuit 110 and low voltage system electronics 150. In at least one embodiment, a chip 140-3 from Silicon Labs is employed (model number Silicon Labs 8450, available from Silicon Labs, Silicon Labs 8450, Silicon Laboratories, Inc., Sunnyvale, Calif.). The chip 140-3 provides up to 2500 Volts Root Mean Square (VRMS) isolation between the signals on either side of the isolation boundary (i.e., between signals on 142 and signals on 144). Other vendors provide similar chips. The isolation IC 140-3 can be used with a different connection scheme to propagate signals in either direction across the isolation boundary.

Figure 4D:
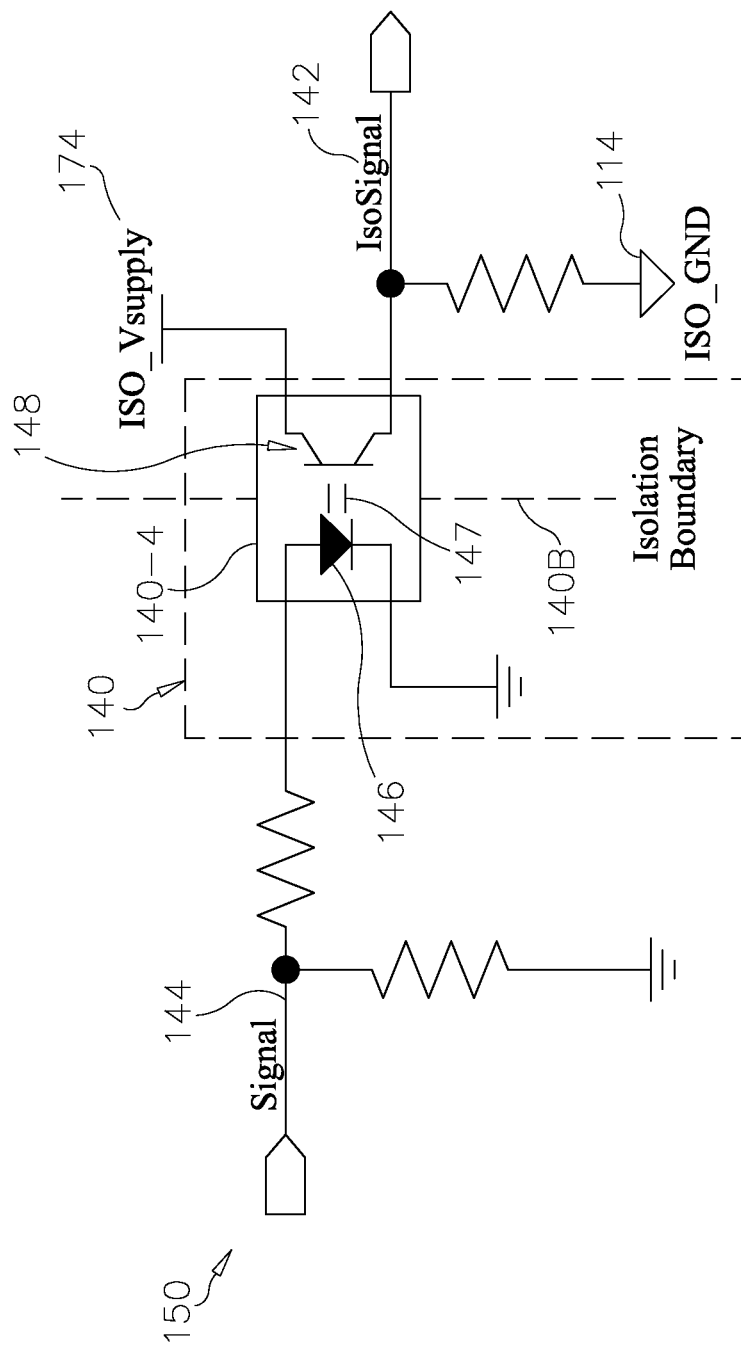
FIG. 4D is a schematic representation of circuitry that may be included in isolation circuitry according to another embodiment of the present invention.

FIG. 4D is a schematic representation of isolation circuitry that may be used in 140 according to another embodiment of the present invention. In this embodiment, an opto-isolator 140-4 is used to propagate signals across the isolation boundary 140B of isolation circuitry 140. The input signal 144 turns on an LED 146 which produces photons 147 which leads to base current from photosensitive structures in the base region of a bipolar photo-transistor 148. The base current then turns the transistor 148 on which recreates the input signal as an isolated signal 142 on the isolated side of the isolation boundary.

Figure 4F:
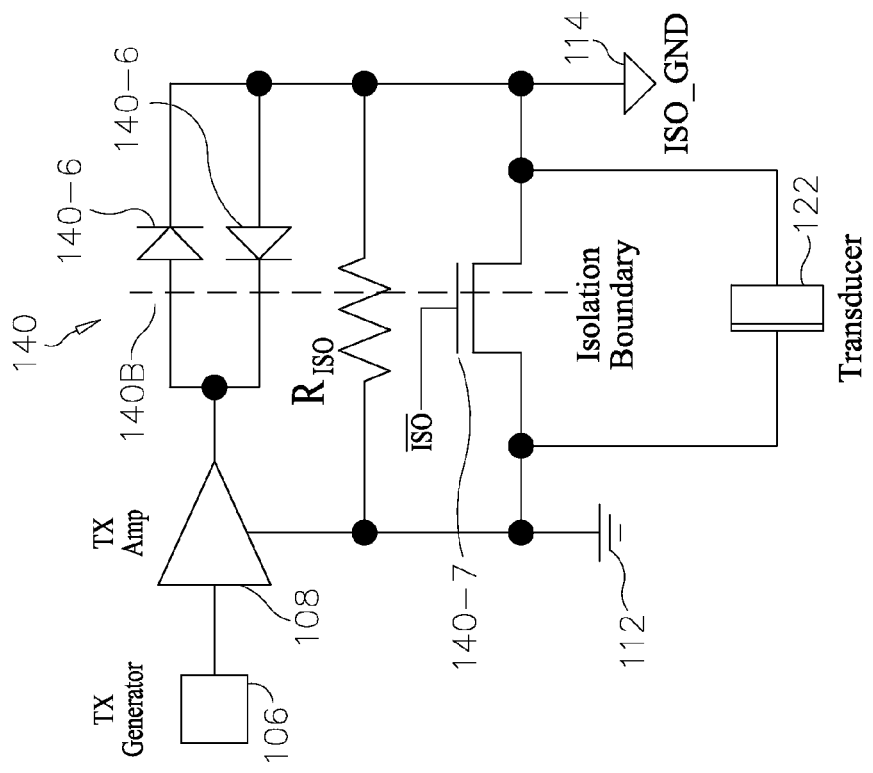
FIG. 4F is a schematic representation of circuitry that may be included in isolation circuitry according to another embodiment of the present invention.
Figure 4E:
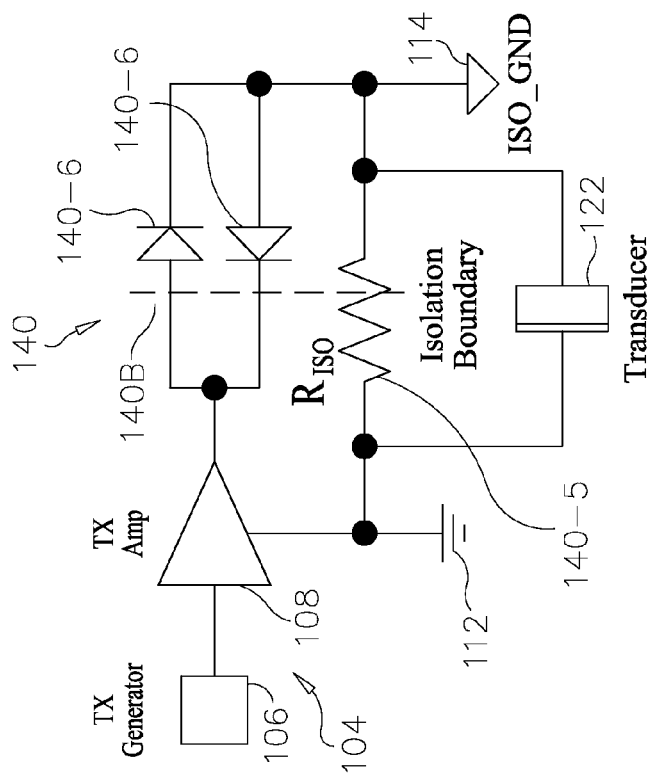
FIG. 4E is a schematic representation of a circuit that may be included in isolation circuitry 140 according to another embodiment of the present invention.

FIG. 4E is a schematic representation of a circuit that may be included in isolation circuitry 140 according to another embodiment of the present invention. System ground 112 and isolated local ground 114 can be isolated by a resistor 140-5 and diodes 140-6 act as the switching element 136 to isolate the high voltage transmit when it is inactive. FIG. 4E shows a simplified circuit diagram highlighting the relationships between the grounds 112, 114, the transmit circuit 104 and the transducer array 122. If the resistor ($R_{ISO}$) 140-5 has a high impedance compared to the impedance of the transducer 120/transducer array 122 at the transmit frequency, the ISO_GND 114 is easily driven to the transmit voltage by the Transmit (TX) amplifier 108. The resistance of $R_{ISO}$ 140-5 needs to be large compared to the transducer impedance but small enough to provide minimal voltage drop for the DC current path between ISO_GND 114 and system ground 112. For example, if a large area transducer array 122 has a 2 ohm center frequency impedance and the average DC current is 1 mA, an $R_{ISO}$ of 5 ohms would add minimal load to the transmit amplifier and still only have a 5 mV DC voltage drop. Optionally, a matching network can be introduced between the transmit amplifier and the transducer to compensate for the complex impedance of the transducer, as described above.

If the particular impedances in the system do not lead to an appropriate value of $R_{ISO}$, a switch (or a combination of switches) can be added as shown in FIG. 4F. FIG. 4F shows an embodiment in which a field effect transistor (FET) 140-7 is configured as a switch, such that FET-7 is turned off only during the transmit events. In this manner a low impedance ground return path is maintained during the receive operation when the transmit is inactive.

Figure 6:
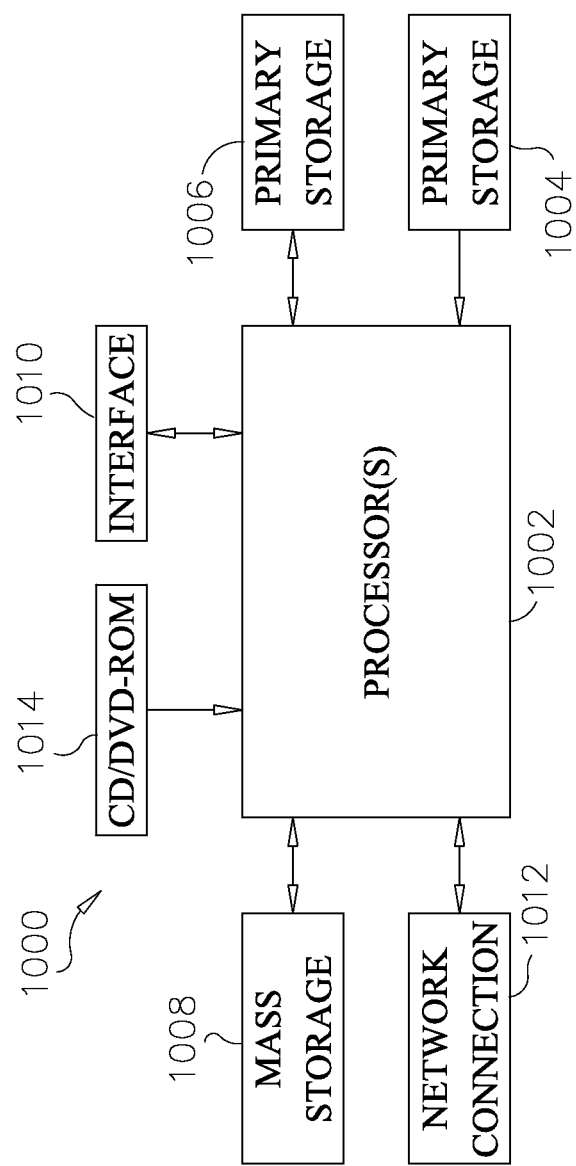
FIG. 6 is a block diagram of a computer system that may be implemented in a system according to an embodiment of the present invention.

FIG. 6 is a block diagram of a computer system 100 that may be implemented in a system according to an embodiment of the present invention. This figure represents a typical computer system, components of which, or all of which may be employed in a system according to the present invention. For example, all or components shown in FIG. 6 may be employed in the host computer 1000 shown in FIGS. 2 and 3. The computer system 1000 includes any number of processors 1002 (also referred to as central processing units, or CPUs, that are coupled to storage devices including primary storage 1006 (typically a random access memory, or RAM), primary storage 1004 (typically a read only memory, or ROM). As is well known in the art, primary storage 1004 acts to transfer data and instructions uni-directionally to the CPU and primary storage 1006 is used typically to transfer data and instructions in a bi-directional manner. Both of these primary storage devices may include any suitable computer-readable media such as those described above. A mass storage device 1008 is also coupled bi-directionally to CPU 1002 and provides additional data storage capacity and may include any of the computer-readable media described above. Mass storage device 1008 may be used to store programs, data and the like and is typically a secondary storage medium such as a hard disk that is slower than primary storage. It will be appreciated that the information retained within the mass storage device 1008, may, in appropriate cases, be incorporated in standard fashion as part of primary storage 1006 as virtual memory. A specific mass storage device such as a CD-ROM or DVD-ROM 1014 may also pass data uni-directionally to the CPU.

CPU 1002 is also coupled to an interface 1010 that includes one or more input/output devices such as video monitors, track balls, mice, keyboards, microphones, touch-sensitive displays, transducer card readers, magnetic or paper tape readers, tablets, styluses, voice or handwriting recognizers, or other well-known input devices such as, of course, other computers. Interface 1010 may include interfaces to low voltage system electronics 50 and/or high voltage transmit circuit 104, etc. Finally, CPU 1002 optionally may be coupled to a computer or telecommunications network using a network connection as shown generally at 1012. With such a network connection, it is contemplated that the CPU might receive information from the network, or might output information to the network in the course of performing its functions. The above-described devices and materials will be familiar to those of skill in the computer hardware and software arts.

Figure 7:
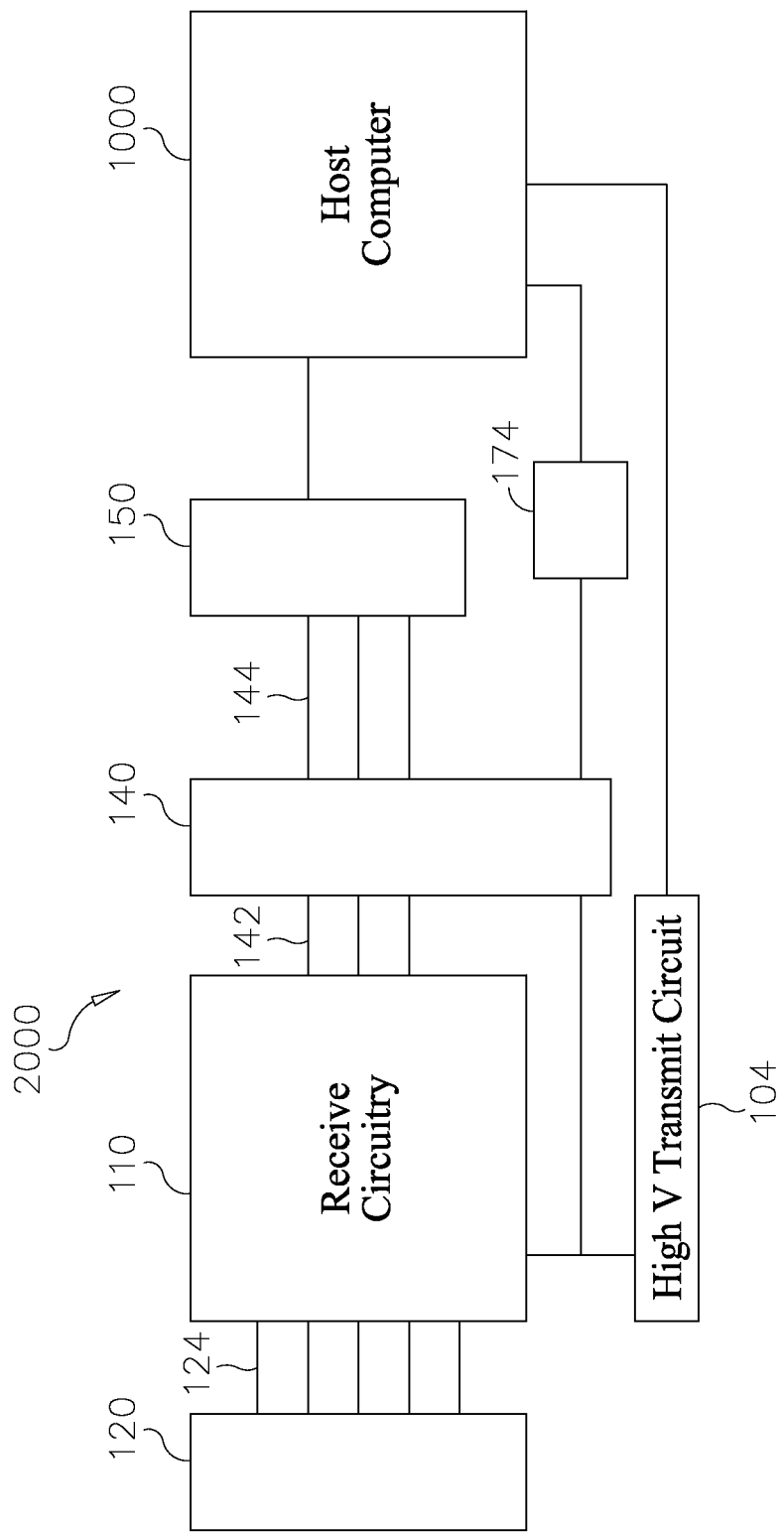
FIG. 7 is a block diagram of an ultrasonic imaging system employing a floating transducer drive according to an embodiment of the present invention.

FIG. 7 is a block diagram of an ultrasonic imaging system 2000 employing a floating transducer drive 100 according to an embodiment of the present invention, illustrating interconnection of transducer array 120, receive circuitry 110, high voltage transmit circuitry 104, isolation circuitry 130, low voltage system electronics 150, power supply 174 and host computer 1000, as described previously.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A floating transducer drive comprising:
a receive circuit electrically connected to an isolated local ground;
a relatively high-voltage transmit circuit;
a transducer;
a system ground;
a relatively low-voltage processing circuit; and
isolation circuitry configured such that during a transmit event during which the relatively high voltage transmit circuit sends a relatively high voltage signal to said transducer, said isolated local ground is electrically connected to said transmit circuit; and wherein said isolation circuitry is configured such that when said transmit event is not occurring, said isolated local ground is electrically connected to said system ground.

2. The floating transducer drive of claim 1, wherein said isolation circuitry further comprises an isolation circuit electrically connected between said receive circuit and said relatively low-voltage processing circuit.

3. The floating transducer drive of claim 1, wherein said isolation circuitry further comprises a transducer switch switchable from a receive position in which said transducer switch electrically connects said transducer to said receive circuit, to a transmit position in which said transducer switch electrically connects said transducer to said isolated local ground;
wherein, when said transducer switch is in said receive position, said isolated local ground is electrically connected to said system ground; and
wherein, when said transducer switch in in said transmit position, said isolated local ground is electrically connected to said transmit circuit.

4. The floating transducer drive of claim 1, wherein said isolation circuitry comprises an isolation switch switchable from a ground position in which said isolation switch electrically connects said isolated local ground to said system ground, to a transmit position in which said isolation switch electrically connects said isolated local ground to said transmit circuit.

5. The floating transducer drive of claim 4, wherein said isolation switch disconnects said transmit circuit from said isolated local ground when in said ground position; and
wherein said isolation switch disconnects said isolated local ground from said system ground when in said transmit position.

6. The floating transducer drive of claim 1, further comprising a relatively low value resistor electrically connecting said isolated local ground to said system ground.

7. The floating transistor drive of claim 6, further comprising a matching network electrically connecting said transmit circuit to said isolated local ground.

8. The floating transducer drive of claim 3, wherein said transducer comprises a plurality of transducers, and said transducer switch comprises a plurality of transducer switches at least equal to a number of said transducers.

9. The floating transducer drive of claim 1, wherein said isolation circuitry comprises at least one isolation element comprising at least one of a resistor, a diode, a transformer, or an integrated circuit isolator.

10. The floating transducer drive of claim 1, wherein said isolation circuitry comprises at least one isolation element, each said isolation element including a component selected from the group consisting of: at least one resistor, at least one diode, at least one transformer, and at least one integrated circuit isolator.

11. The floating transducer drive of claim 1, wherein said receive circuit comprises a sample-and-hold connectable receivably to said transducer for sampling an incoming signal from said transducer and outputting an amplitude of said incoming signal.

12. The floating transducer drive of claim 11, wherein said receive circuit comprises an analog-to-digital converter connected receivably to said sample-and-hold for assigning a digital value to said amplitude and outputting said digital value.

13. The floating transducer drive of claim 12, wherein said receive circuit comprises a memory connected receivably to said analog-to-digital converter for storing said digital value and outputting said digital value.

14. The floating transducer drive of claim 1, wherein said receive circuit comprises an amplifier connectable receivably to said transducer for amplifying an incoming signal received from said transducer.

15. The floating transducer drive of claim 14, wherein said amplifier includes at least one filter for filtering said incoming signal.

16. The floating transducer drive of claim 14, wherein said receive circuit further comprises a pre-amplifier for amplifying said incoming signal and outputting an amplified incoming signal to said amplifier.

17. The floating transducer drive of claim 1, wherein said transducer is configured to convert a wave received to an incoming signal and to output said incoming signal to said receive circuit.

18. The floating transducer drive of claim 17, wherein said incoming signal is a signal selected from the group consisting of: an electro-magnetic signal; an electric signal; and an optical signal.

19. A method of driving an ultrasound transducer, said method comprising:
 electrically connecting a relatively high voltage transmit circuit to the transducer;
 locally grounding a receive circuit via an isolated local ground;
 sending a relatively high voltage outgoing signal from said relatively high voltage transmit circuit to the transducer;
 transducing said outgoing signal to outgoing waves;
 receiving at least a portion of said outgoing waves as reflected waves reflected back to said transducer;
 transducing said reflected waves to an incoming signal;
 inputting said incoming signal to said receive circuit;
 converting said incoming signal by said receive circuit to a digital signal;
 outputting said digital signal to an isolation circuit; and
 outputting a relatively low voltage, isolated signal to a relatively low-voltage processing circuit.

20. The method of claim 19, further comprising connecting said isolated local ground to a relatively high voltage transmit circuit during performance of said sending a relatively high voltage outgoing signal from said relatively high voltage transmit circuit to the transducer, wherein said high voltage outgoing signal is carried to the transducer via the isolated local ground.

21. The method of claim 19, further comprising connecting said isolated local ground to a system ground during performance of said inputting said incoming signal to said receive circuit.

22. The method of claim 19, wherein a relatively low value resistor electrically connects said isolated local ground to a system ground.

23. The method of claim 22, wherein a matching network electrically connects said transmit circuit to said isolated local ground.

24. The method of claim 23, wherein said matching network electrically connects said transmit circuit to said system ground via said relatively low value resistor.

25. A sub-system for controlling switching between transmit and receive operations in an ultrasound imaging system, said sub-system comprising:
 a relatively high voltage transmit circuit; a receive circuit electrically connected to an isolated local ground;
 a transducer configured to transduce an outgoing signal received from said relatively high voltage transmit circuit to outgoing ultrasound and to transduce incoming ultrasound reflected back to said transducer to an incoming signal and to output said incoming signal to said receive circuit;
 a sub-system ground;
 a transducer switch switchable from a receive position in which said transducer switch electrically connects said transducer to said receive circuit, to a transmit position in which said transducer switch electrically connects said transducer to said isolated ground;
 a relatively low-voltage processing circuit; and an isolation circuit electrically connected between said receive circuit and said relatively low-voltage processing circuit;
 wherein, when said transducer switch is in said receive position, said isolated local ground is electrically connected to said system ground; and
 wherein, when said transducer switch in in said transmit position, said isolated local ground is electrically connected to said transmit circuit.

26. An ultrasonic imaging system comprising:
 a system ground;
 a transducer;
 a receive circuit operatively connectable to said transducer and electrically connected to an isolated local ground;
 a transmit circuit operatively connectable to said transducer; and
 a host computer operatively connected to said receive circuit;
 wherein said receive circuit floats when said transmit circuit sends a transmit pulse to said transducer, such that said receive circuit avoids receiving a voltage potential difference between the relatively high voltage transmit circuit and the system ground.

27. The system of claim 26, further comprising:
 a transducer switch switchable from a receive position in which said transducer switch electrically connects said transducer to said receive circuit, to a transmit position in which said transducer switch electrically connects said transducer to said transmit circuit;
 a relatively low-voltage processing circuit; and
 an isolation circuit electrically connected between said receive circuit and said relatively low-voltage processing circuit;
 wherein, when said transducer switch is in said receive position, said isolated local ground is electrically connected to said system ground; and
 wherein, when said transducer switch is in said transmit position, said isolated local ground is electrically connected to said transmit circuit.

* * * * *